United States Patent [19]
Rothschild et al.

[11] Patent Number: 6,146,349
[45] Date of Patent: *Nov. 14, 2000

[54] NATURAL FOOT ORTHOSIS AND METHOD OF MANUFACTURING THE SAME

[75] Inventors: Vernon R. Rothschild, Berlin; John R. Fox, Trappe; Russell J. Rothschild, Kent Island; Kelly Ann Rothschild, Berlin, all of Md.

[73] Assignee: Rothschild's Orthopedics, Salisbury, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/753,929

[22] Filed: Dec. 3, 1996

Related U.S. Application Data

[63] Continuation-in-part of application No. 08/707,489, Sep. 19, 1996, abandoned.

[51] Int. Cl.[7] .......................................................... A61F 5/00
[52] U.S. Cl. ...................................... 602/27; 602/5; 602/6
[58] Field of Search ................................. 602/23, 27, 28, 602/29, 6–8; 264/222, 223

[56] References Cited

U.S. PATENT DOCUMENTS

| | | |
|---|---|---|
| 3,680,549 | 8/1972 | Lehneis et al. |
| 4,454,871 | 6/1984 | Mann et al. |
| 4,489,034 | 12/1984 | Davison |
| 5,312,669 | 5/1994 | Bedard |
| 5,368,549 | 11/1994 | McVicker |
| 5,520,628 | 5/1996 | Wehr ......................................... 602/27 |
| 5,573,501 | 11/1996 | Ruscito et al. ............................. 602/7 |

FOREIGN PATENT DOCUMENTS 1298930  12/1972  United Kingdom.

OTHER PUBLICATIONS

Great Britain Search Report dated Jan. 15, 1998.

*Primary Examiner*—Richard J. Apley
*Assistant Examiner*—Jayne Saydah
*Attorney, Agent, or Firm*—Nixon Peabody, LLP; Donald R. Studebaker

[57] ABSTRACT

A copolymer thermoplastic natural foot orthosis for supporting and controlling the movement of a lower extremity and method for manufacturing the same. The orthosis is fabricated by forming a positive mold of the lower extremity, and modifying the positive mold in predetermined locations to accomplish the type of lower extremity control desired. A strip of heated thermoformable copolymer material is strategically positioned around predetermined locations on the positive mold for providing increased support for the natural foot orthosis at these predetermined locations. A sheet of heated thermoformable copolymer material is then drape mold around the positive mold and copolymer strip, wherein the copolymer sheet is vacuum sealed to conform to the shape of the positive mold. During the vacuum formation process, the copolymer sheet and copolymer strip combine together so that the copolymer sheet and copolymer strip are integrally formed into a single supporting structure. After the thermoformed copolymer sheet and strip have cooled, strategically positioned trimlines are made in the thermoformed copolymer sheet depending upon the lower extremity control desired, wherein all excess material outside of the trimlines is removed. Utilizing modifications to the positive mold and strategically positioned trimlines in conjunction with the reinforcing copolymer strip, a natural foot orthosis is achieved that is lighter, cosmetically superior, dynamic and durable.

7 Claims, 10 Drawing Sheets

NATURAL FOOT ORTHOSIS AND METHOD OF MANUFACTURING THE SAME

This application is a continuation-in-part of U.S. patent application Ser. No. 08/707,489, filed Sep. 19, 1996, now abandoned.

BACKGROUND OF THE INVENTION

1. Technical Field

The present invention relates generally to orthotic devices for limiting the motion of a limb. More particularly, the present invention relates to a natural foot orthosis for supporting and controlling the movement of a foot of the wearer of the orthosis and a method of fabricating the orthosis.

2. Background Art

The use of orthotic devices to help support and control the movement of the joints of the lower extremities has been a long established practice. Conventionally, when a person injures or loses motor control of their foot, orthotic devices are often used to brace and rehabilitate the foot. One such condition requiring the use of an orthotic device is when a person is unable to lift a foot, otherwise known as drop foot. Drop foot may be the result of brain damage from a stroke or cardiovascular accident, spinal injury, hereditary motor and sensory neuropathies, or neuromuscular disease. Additionally, any damage to the muscle and nerves which activate the muscle of the neuromuscular system related to the foot may cause drop foot.

The neuromuscular system of the foot comprises the dorsiflexor muscles which are those on the front of the leg and below the knee which lift the foot. The action of lifting the foot from a position substantially aligned with the lower leg to a position substantially perpendicular to the lower leg is known by the term dorsiflexion, while the action of extending the foot from a position substantially perpendicular to the lower leg to a position substantially aligned with the lower leg is known by the term plantar flexion. If the dorsiflexors are weak, a person will be unable to lift the foot as required in the swing phase of a step. The inability to lift the foot may cause a person to trip, since the foot may make contact with the ground during the downward swing of the leg.

In order to prevent drop foot, a type of brace or orthosis known as an Ankle Foot Orthosis (AFO) has been used to compensate for weak dorsiflexors by resisting plantar flexion at heel strike and during swing phase. Until the early 1960's, lower extremity bracing was essentially accomplished using metal, first steel and later the lighter aluminum. In the late 1960's, plastic began to be used for orthotic devices, initially laminates and then, as in the case today, thermoplastics. The most prevalent AFO utilized today is the posterior leaf-spring orthosis, which is typically fabricated by molding sheet plastic over a positive mold of a person's extremity. A posterior leaf-spring orthosis is typically a thermoplastic rigid 90° brace made to fit inside of a shoe. The mobility of an ankle held within the posterior leaf-spring orthosis is determined by the trim lines forming the shape of the orthosis and also by the thickness of the plastic. Another important component determining the mobility of the ankle is the attitude of the extremity when the cast was taken, i.e. dorsi-flexed, neutral, or planter-flexed, as well as the particular shoe to be worn taking into account the heel height.

U.S. Pat. No. 5,370,604 issued to Bernardoni discloses one such example of a posterior leaf-spring AFO which assists a person suffering from drop foot, wherein the AFO is formed form a thermoformed polypropylene material. While polypropylene AFO's have the advantage that they can be mass-manufactured and modified after fabrication to ensure a proper fit, until now AFO's constructed of unreinforced polypropylene were too flexible to provide sufficient dorsiflexion assistance. In order to overcome the flexibility of polypropylene, some polypropylene AFO's incorporated corrugations into their posterior surface and extending downward on their medial and lateral surfaces to add strength and stability to the AFO.

The posterior leaf-spring orthosis, however, has the limitation of restricting normal and desirable ankle and knee motion. For instance, an overzealous attempt to prevent drop foot by increasing the dorsiflexion attitude of the orthosis also has the effect of making the knee joint unstable by inhibiting knee extension. Without changing the attitude of the orthosis, the thickness of the posterior leaf-spring orthosis must be increased to provide the additional support to prevent drop foot. However, since the posterior leaf-spring orthosis fits within the shoe of the wearer, the thickness of the orthosis is limited by the available space between the wearer's foot and the shoe.

Therefore, alternative designs for an orthosis have been developed which were superior to the posterior leaf-spring orthosis in that they prevented drop foot and controlled mild to moderate inversion and eversion, while still allowing more normal ankle and knee articulation. Such alternative designs include spiral and hemi-spiral AFO's. These alternative designs have also been manufactured from thermoformable plastic material to maintain the light weight of the AFO. Although these alternative AFO's are preferred by patients due to their more functional, lighter, and energy saving design, this type of bracing was abandoned by most orthotists due to material failure and breakage problems. Once again, the plastic material used to form these orthotic devices is either to flexible to provide adequate support or too brittle to withstand wear and tear without suffering breakage problems.

Accordingly, there is clearly a need for a lower extremity orthotic device having a lighter, cosmetically superior, and dynamic design which is more durable and does not experience material failure through normal use.

SUMMARY OF THE INVENTION

It is a primary object of the present invention to overcome the aforementioned shortcomings associated with the prior art.

Another object of the present invention is to provide a natural foot orthosis which adequately supports a lower extremity while still allowing normal ankle and knee articulation.

Yet another object of the present invention is to provide a more durable natural foot orthosis for supporting a lower extremity which does not experience material failure through normal use of the natural foot orthosis.

A further object of the present invention is to provide a natural foot orthosis for supporting a lower extremity fabricated from a co-polymer material which resists material failure while maintaining a light, dynamic, and durable orthosis.

It is a further object of the present invention to provide a natural foot orthosis for supporting a lower extremity which is formed using a method which combines together strategically positioned co-polymer segments so that the co-polymer segments integrally form together in the molding process.

It is yet another object of the present invention to provide a natural foot orthosis for supporting a lower extremity which utilizes modifications to a cast of the lower extremity and predetermined trimlines in forming the orthosis to achieve an orthosis that is lighter, cosmetically superior, dynamic, and durable.

Yet a further object of the present invention is to provide a natural foot orthosis for supporting a lower extremity which controls drop foot, as well as varus or valgus control, while allowing a smooth transition from heel strike to toe off without inhibiting normal ankle or knee articulation.

These as well as additional objects and advantages of the present invention are achieved by providing a natural foot orthosis formed from a thermoformable co-polymer material having strategically positioned locations on the orthosis where additional thermoformable co-polymer material is formed depending upon the type of lower extremity control desired. The natural foot orthosis is formed by initially forming a positive mold of the lower extremity. The positive mold is then modified by adding material or removing material in predetermined locations on the mold depending upon the type of lower extremity control desired. A strip of heated thermoformable copolymer material is then strategically positioned around predetermined locations on the positive mold for providing increased support for the natural foot orthosis at these predetermined locations. A sheet of heated thermoformable copolymer material is next draped around the positive mold and the strategically positioned copolymer strip, wherein the copolymer sheet is vacuum formed around the positive mold so as to conform to the shape of the positive mold. During the vacuum formation process, the copolymer sheet and copolymer strip combine together so that the copolymer sheet and copolymer strip are integrally formed into a single supporting structure.

After the thermoformed copolymer sheet and strip have cooled, strategically positioned trimlines are made in the thermoformed copolymer sheet depending upon the lower extremity control desired, wherein all excess material outside of the trimlines is removed. Utilizing modifications to the positive mold and strategically positioned trimlines, an orthosis is achieved that is lighter, cosmetically superior, dynamic and durable. In addition to controlling drop foot, varus and valgus can also be controlled by creating a three point pressure system in the natural foot orthosis. For varus control, there are two pressure points created on the medial side of the lower extremity while one pressure point is created on the lateral side of the lower extremity at a point between the two medial pressure points. For valgus control, there are two pressure points created on the lateral side of the lower extremity while one pressure point is created on the medial side of the lower extremity at a point between the two lateral pressure points.

The thermoformable copolymer sheet and strip are preferably formed from a copolymer material having a ratio of approximately 90-10 polypropylene to polyethylene or approximately 93-7 polypropylene to polyethylene, as these specific copolymers have been found to resist material failure while also providing a light and dynamic orthosis.

DETAILED DESCRIPTION OF THE PREFERRED EMBODIMENT

Figure 1:
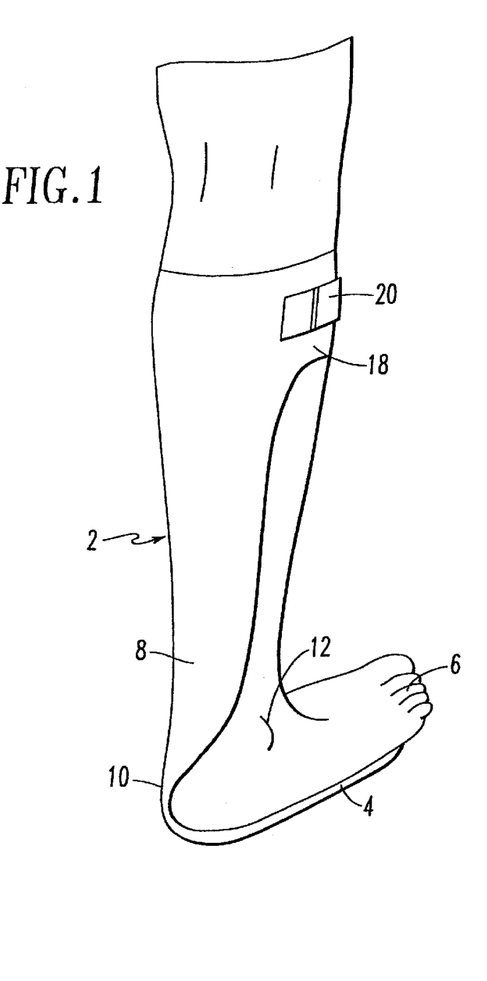
FIG. 1 is a perspective view of one embodiment of the natural foot orthosis of the present invention shown positioned on a lower extremity a right leg of a patient.
Figure 2A:
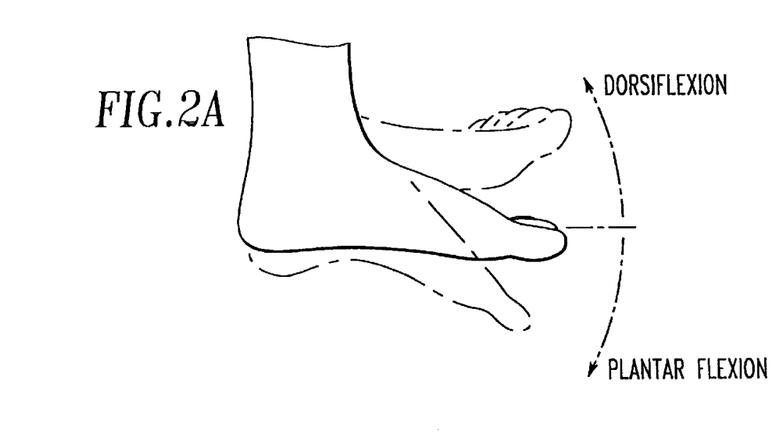
FIG. 2(A) is a side view of a foot illustrating the dorsiflexion and plantar flexion movement of the foot.
Figure 2B:
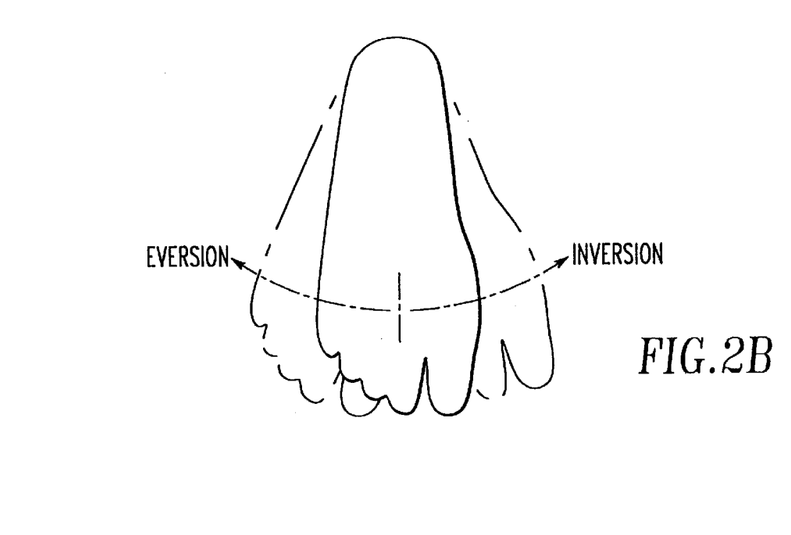
FIG. 2(B) is a front view of a foot illustrating inversion and eversion movement of the foot.
Figure 3A:
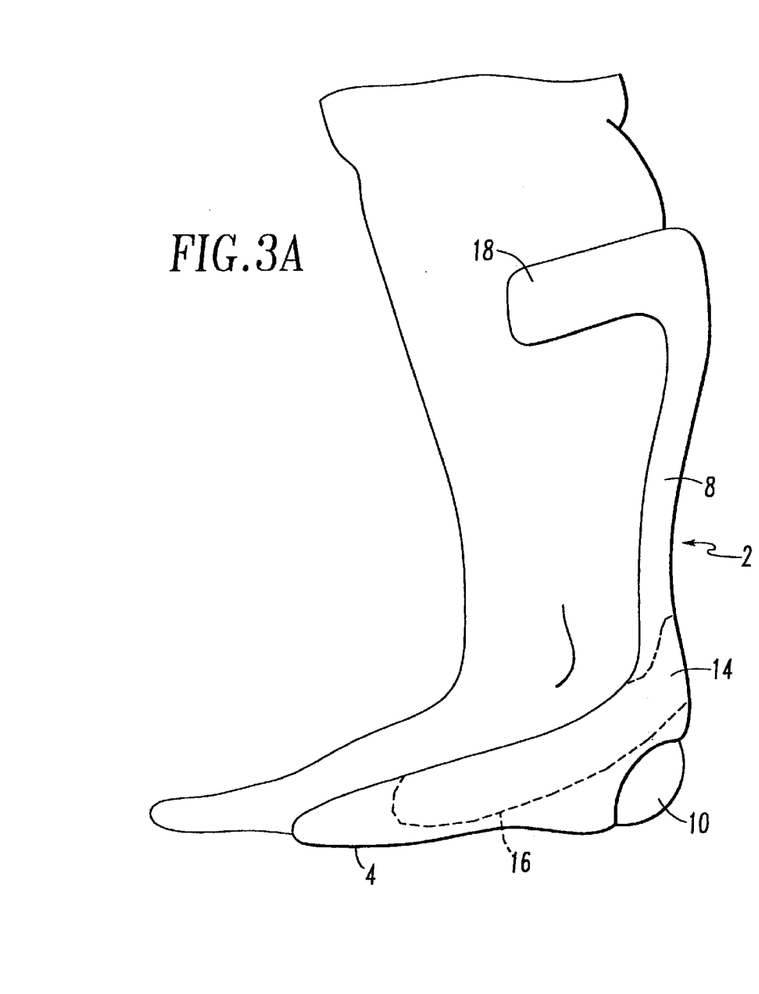
FIGS. 3(A)–3(D) are medial, lateral, frontal, and posterior views of the natural foot orthosis of FIG. 1, respectively.
Figure 3B:
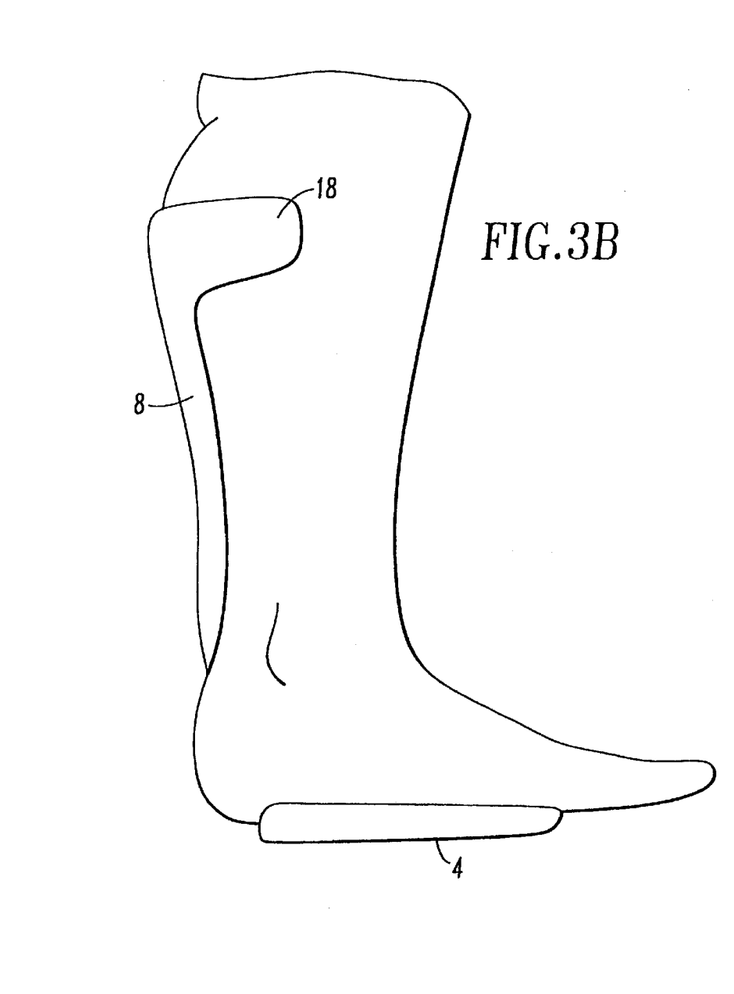
Figure 3C:
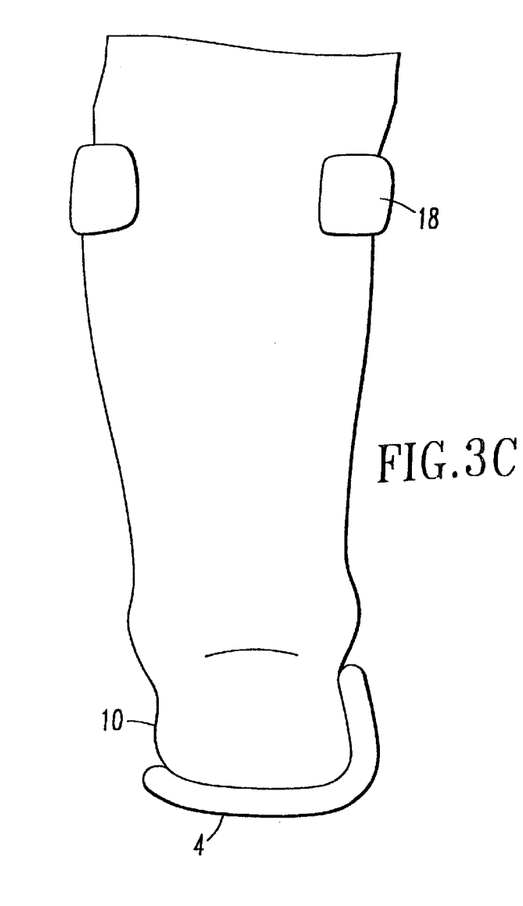
Figure 3D:
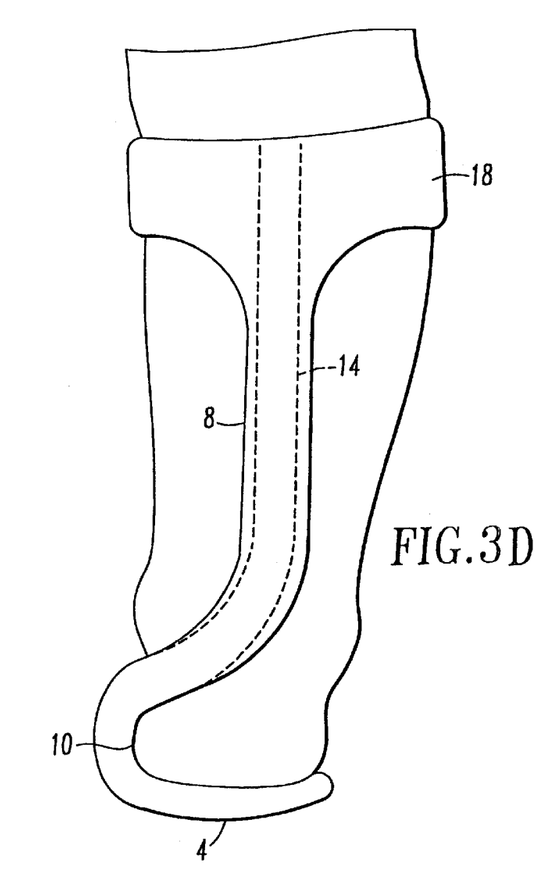

Referring now to FIG. 1, a perspective view of one embodiment of the natural foot orthosis (N.F.O.) 2 of the present invention is shown positioned on a lower extremity. The natural foot orthosis 2 includes a foot plate 4 which extends beneath the bottom of a foot 6, wherein foot plate 4 is connected to a calf portion 8 which extends from foot plate 4 around the medial side 10 of the ankle and up the calf of the lower extremity. The lateral side 12 of the ankle is substantially not covered by the natural foot orthosis 2 in this embodiment. The primary function of the embodiment of the natural foot orthosis 2 shown in FIG. 1 is to prevent drop foot by resisting plantar flexion at heel strike and during swing phase. As illustrated in FIG. 2(A), plantar flexion occurs when the foot 6 is extended from a position substantially perpendicular to the lower leg to a position substantially aligned with the lower leg. Therefore, foot plate 4 must maintain its rigidity and not rotate with respect to calf portion 8 in order to resist plantar flexion. Further, alternative embodiments of the present invention, which will be described in detail hereinafter, will also prevent eversion and inversion of the foot 6, wherein such movement of the foot 6 is illustrated in FIG. 2(B). In order to resist eversion and inversion, once again, foot plate 4 must maintain its rigidity and not rotate with respect to calf portion 8.

In order to provide added support for the natural foot orthosis 2, a reinforcing strip of thermoplastic material is strategically positioned around the natural foot orthosis 2 at predetermined locations to provide the additional control desired. Referring now to FIGS. 3(A)–3(D), the natural foot orthosis 2 of FIG. 1 is illustrated in its application on the right leg of a patient from a medial view, lateral view, front view, and posterior view, respectively. As indicated by the dashed lines, a thermoplastic strip 14 extends from a longitudinal arch 16 of the natural foot orthosis 2 below the malleoli posterior and curves around to the back of the orthosis 2. The thermoplastic strip 14 extends the length of calf section 8 centered proximal over the edge of the orthosis 2. The thermoplastic strip 14 is integrally formed with the thermoplastic material comprising foot plate 4 and calf portion 8, so that the thermoplastic material comprising foot plate 4 and calf portion 8 and thermoplastic strip 14 are blended together to form a unitary supporting structure for the natural foot orthosis 2. By forming the natural foot orthosis 2 with the reinforcing thermoplastic strip 14 marrying or blending together with the remaining thermoplastic material constituting the natural foot orthosis 2, a stronger and more durable orthosis can be manufactured which remains light and allows normal ankle and knee articulation. The natural foot orthosis 2 also includes a calf band 18 for retaining the natural foot orthosis 2 to the upper portion of the lower extremity, wherein the calf band 18 may include a fastening device 20, such as a fastenable strap, which extends around the front portion of the lower extremity to hold the calf band 18 against the lower extremity.

The natural foot orthosis 2 of the present invention is manufactured from a thermoformable plastic material. The extent to which motion is controlled depends primarily on the relative rigidity of the plastic material, which in turn depends upon 1) its chemical composition, 2) thickness, and 3) shape, which includes trim lines and reinforcements. The natural foot orthosis 2 of the present invention utilizes the optimal chemical composition, thickness, reinforcement, and shape to provide an orthosis which is lighter, cosmetically superior, dynamic and durable.

The natural foot orthosis 2 is preferably fabricated from a copolymer material having a ratio of approximately 90-10 polypropylene to polyethylene or approximately 93-7 polypropylene to polyethylene. The inventors of the present invention have found copolymers of such composition to be advantageous over other copolymer compositions in that natural foot orthosis 2 formed with these specific ratios of polypropylene to polyethylene were superior in resisting material failure and breakage problems. Furthermore, copolymer materials used previously were either too rigid and prone to cracking or were too soft not having enough memory and possessing too much flexibility. The copolymer composition used in the present invention in forming the natural foot orthosis 2 has been found to possess a good balance of memory, rigidity, and flexibility. While ratios of approximately 90-10 and 93-7 polypropylene to polyethylene have been found to possess these optimal characteristics, other copolymer compositions may be used in conjunction with the formation process of the present invention as long as they also contain the balance between memory, rigidity, and flexibility. Additionally, sheets of these specific copolymers have been found to blend together well, which is necessary as the present invention marries together a copolymer reinforcing strip with a copolymer sheet during the formation process to achieve the natural foot orthosis 2.

Figure 4:
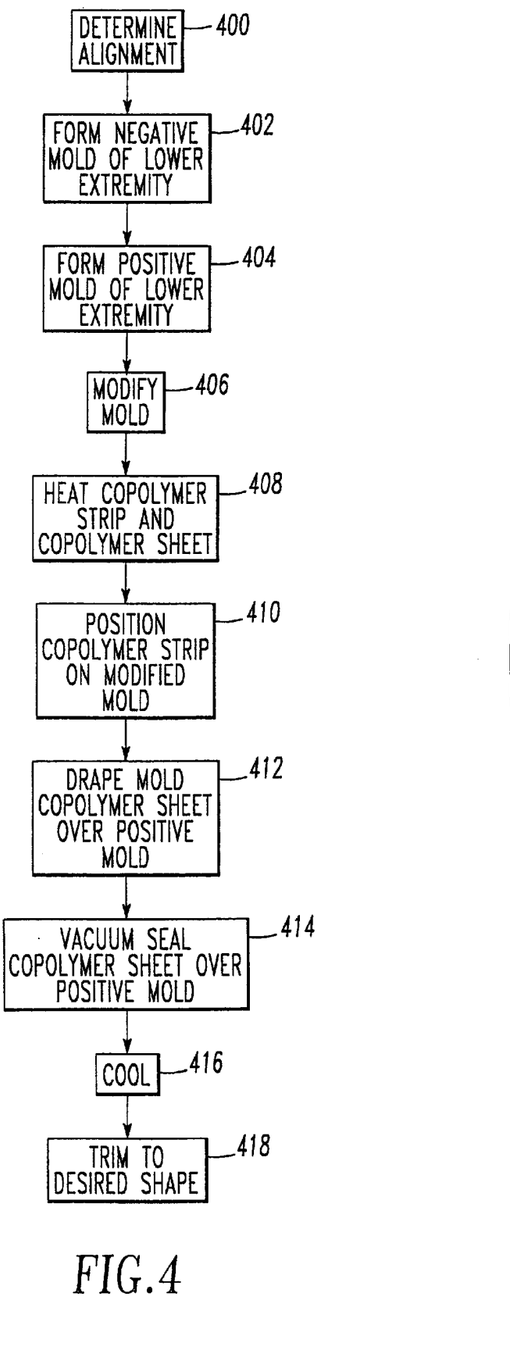
FIG. 4 is a flow chart of a method for fabricating the natural foot orthosis of the present invention.

Referring now to FIG. 4, the method of forming the natural foot orthosis 2 in accordance with the present invention is shown. Initially in step 400, the person's lower extremity is evaluated to determine the desired alignment of the natural foot orthosis 2, such as varus, valgus, plantar flexion, or dorsiflexion control. Then, in step 402, a negative cast is formed of the lower extremity in any of the manner conventionally used in the field. In step 404, the negative cast is filled with a formable material such as plaster to obtain a positive mold of the lower extremity. After the negative cast is poured and prior to hardening, a hollow pipe is inserted into the plaster positive mold. The positive mold is then modified in step 406 by adding material or removing material in predetermined locations on the positive mold depending upon the type of lower extremity control desired.

In order to provide additional strength and rigidity to the natural foot orthosis 2, a strip of heated thermoformable copolymer material is then strategically positioned around predetermined locations on the positive mold in steps 408 and 410 for providing increased support for the natural foot orthosis at these predetermined locations. The thickness of the copolymer strips can be varied to change the strength and support characteristics of the natural foot orthosis 2. In step 412, a sheet of heated thermoformable copolymer material is draped around the positive mold and strategically positioned copolymer strip without distorting or moving the placement of the copolymer strip. The copolymer sheet is then vacuum sealed around the positive mold in step 414, so as to conform to the shape of the positive mold. During the vacuum formation process, the copolymer sheet and the copolymer strip combine together so that the copolymer sheet and copolymer strip are integrally formed into a single supporting structure. After the thermoformed copolymer sheet and strip have cooled in step 416, strategically positioned trimlines are made in the thermoformed copolymer supporting structure depending upon the type of lower extremity control desired. The trimlines will generally extend along both sides of the path of the copolymer strip. In step 418, all excess material outside of the trimlines is removed to complete the formation of the natural foot orthosis 2.

The method of forming the natural foot orthosis 2 of the present invention provides an orthosis which withstands material failure and breakage problems due to its unique formation. By strategically positioning the copolymer strip in predetermined locations where greater support is required, the natural foot orthosis 2 produced is more stable and durable. Furthermore, by causing the copolymer strip and copolymer sheet to combine or marry together during the formation process, a unified support structure is created having greater strength and stability with reinforcement in the areas where the copolymer strip was positioned on the positive mold. Additionally, utilizing modifications to the positive mold and strategically positioned trimlines, a natural foot orthosis 2 is achieved that is lighter, cosmetically superior, dynamic and durable.

This method of forming a natural foot orthosis 2 can be implemented for every type of lower extremity control desired. By strategically positioning the reinforcing copolymer strips and modifying the positive mold of the lower extremity as well as trimming the natural foot orthosis 2 to a desired shape, specific pressure points can be created to act on the lower extremity to achieve the desired control. In addition to controlling drop foot, varus and valgus can also be controlled by creating a three point pressure system in the natural foot orthosis. For varus control, there are two pressure points created on the medial side of the lower extremity while one pressure point is created on the lateral side of the lower extremity at a point between the two medial pressure points. For valgus control, there are two pressure points created on the lateral side of the lower extremity while one pressure point is created on the medial side of the lower extremity at a point between the two lateral pressure points.

Alternatively, the natural foot orthosis 2 may be formed by injection molding, where the thermoformable plastic material is injected into a mold possessing the desired shape and control for the natural foot orthosis 2. In order to obtain reinforcement in the predetermined areas of the natural foot orthosis 2 described above, the mold for the injection molding process possesses predetermined areas having an increased thickness. In this manner, the injection molded natural foot orthosis 2 will be formed as a unitary support structure including reinforced areas having greater strength and support similar to the reinforced areas created in the method of FIG. 4.

Several examples of forming a natural foot orthosis 2 will now be set forth in greater detail for different types of lower extremity control. While these examples are directed to forming a natural foot orthosis 2 using the method set forth above in connection with FIG. 4, the natural foot orthosis 2 may similarly be formed using the injection molding method by forming the injection mold to possess a configuration similar to the final configurations set forth in the foregoing examples. These examples are described merely for the purpose of illustration and do not encompass all possible types of orthosis which may be formed using the method of the present invention.

N.F.O. with Drop Foot Control

Figure 5:
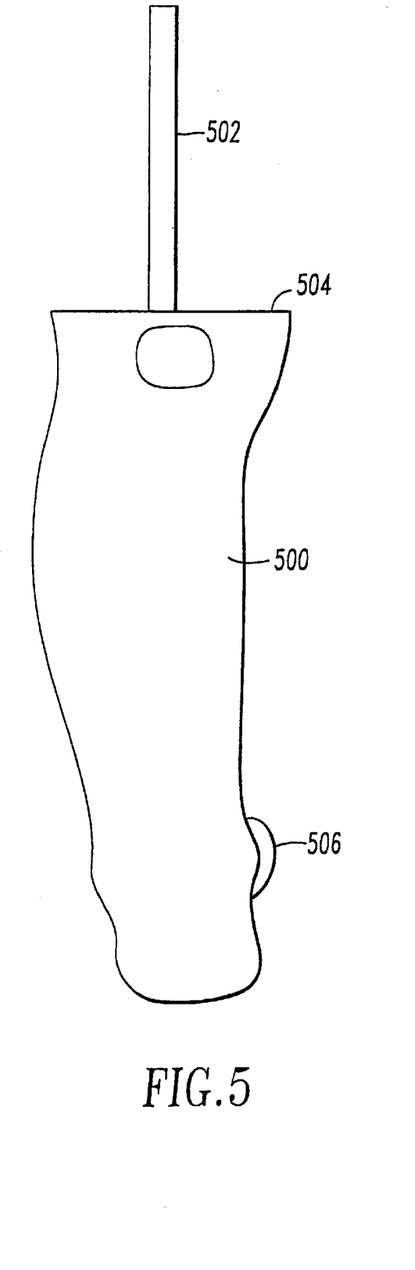
FIG. 5 is a frontal view a positive mold of a right leg of a patient used for forming the natural foot orthosis illustrated in FIGS. 3(A)–3(D).

The embodiment of the natural foot orthosis 2 of the present invention illustrated in FIGS. 3(A)–3(D) is utilized for controlling drop foot. After the most beneficial alignment for controlling drop foot and providing toe lift assist for the specific patient has been determined, a positive mold of the lower extremity is obtained in the manner described above. Referring now to FIG. 5, a frontal view a positive mold 500 of a right leg is shown, where a pipe 502 is inserted into the mold 500 and extends from the proximal end 504 of the mold 500. The positive mold 500 is then modified by adding approximately ⅛ to ¼ inch to the build-up of the mold over the medial malleolus 506. In order to assist in vacuum forming, at least one cotton stockinette is pulled over the positive mold 500, wherein an ⅛ inch of pelite can also be pulled over the positive mold 500 to provide padding within the natural foot orthosis. Alternatively, at least one nylon should be pulled over the dry positive mold 500 if the pelite line is not used. The positive mold 500 is now ready to begin vacuum forming copolymer plastic over the mold 500.

At least one hole is formed in the pipe 502 just above the proximal edge of the mold 500 to allow air to escape from the pipe 502 during the vacuum sealing process. A sheet of copolymer material 3/16 inch thick is cut 6 inches longer than the circumference of the patient's foot and 6 inches longer than the length of the positive mold 500. Additionally, a strip of copolymer material 3/16 inch thick×24 inches long×1¼ wide is also cut. The copolymer strip and copolymer sheet are thermoformable, and are heated in an oven for approximately 15 minutes at 400° F. The distal end of the heated copolymer strip is then centered on the longitudinal arch on the mold 500 and extended below the malleoli posterior above tendon and then curved to the calf section while being centered proximal over the edge of the mold 500.

The heated copolymer sheet is then drape mold over the positive mold 500 having the strategically positioned copolymer strip, wherein the copolymer strip is not moved or distorted while the copolymer sheet is drape mold 500 over the positive mold 500. A vacuum device is then applied to the pipe extending from the proximal end of the positive mold 500, to vacuum seal the copolymer sheet over the positive mold 500. As the copolymer sheet is vacuum formed over the positive mold 500, the heated copolymer sheet and copolymer strip intercombine or marry together into a single structure. The copolymer thermoplastic is then allowed to cool, where it is preferred that artificial means are not used to cool the thermoplastic as they can cause the thermoplastic to become brittle.

After the thermoplastic copolymer has cooled, it is ready to be trimmed into the desired shape for the natural foot orthosis. In order to provide a starting point for trimming, a hole is drilled through the posterior heel of the orthosis ½ inch above the distal aspect of the orthosis. The desired trim lines are marked on the thermoplastic material, wherein the trim lines are formed alongside the copolymer strip for a substantial length of its path. A two inch wide calf band is marked from a point two inches distal of the fibula head and one inch anterior of the lateral midlines. The foot plate 4 is marked approximately at the metatarsal heads, and the reinforcing copolymer strip is marked ⅜ inch on both sides of its length. The foot plate 4 is further marked ⅛ inch above the lateral heel portion of the foot and the mark curves upwards to the posterior drill hole, wherein the reinforcing copolymer strip should remain intact and blend into the arch area. The copolymer thermoplastic material is then cut along the marked lines to trim the excess thermoplastic material from the natural foot orthosis.

N.F.O. with Varus Control

In order to control varus, two pressure points must be created on the medial side of the lower extremity while another pressure point is created on the lateral side of the lower extremity between the two medial pressure points. An alternative embodiment of the natural foot orthosis 600 of the present invention illustrated in FIGS. 6(A)–(D) achieves these three pressure points through its unique design, wherein FIGS. 6(A)–(D) show frontal, lateral, posterior, and medial views of the natural foot orthosis 600, respectively. As can be seen from the figures, the calf portion 602 of the natural foot orthosis 600 extends upward from foot plate 604 along the lateral side of the posterior of the lower extremity, wherein a portion 606 of calf portion 602 is extended around the lateral side of the lower extremity. As indicated by the dashed lines, a thermoplastic reinforcing strip 608 extends from a longitudinal arch in the foot plate 604 and along the path of the calf portion 602, wherein the thermoplastic reinforcing strip 608 is integrally formed with the thermoplastic material comprising foot plate 604 and calf portion 602. The natural foot orthosis 600 resists inversion of the foot by applying two medial pressure points and one lateral on the lower extremity, as indicated by arrows 610, 612, and 614 in FIG. 6(C).

Figure 6A:
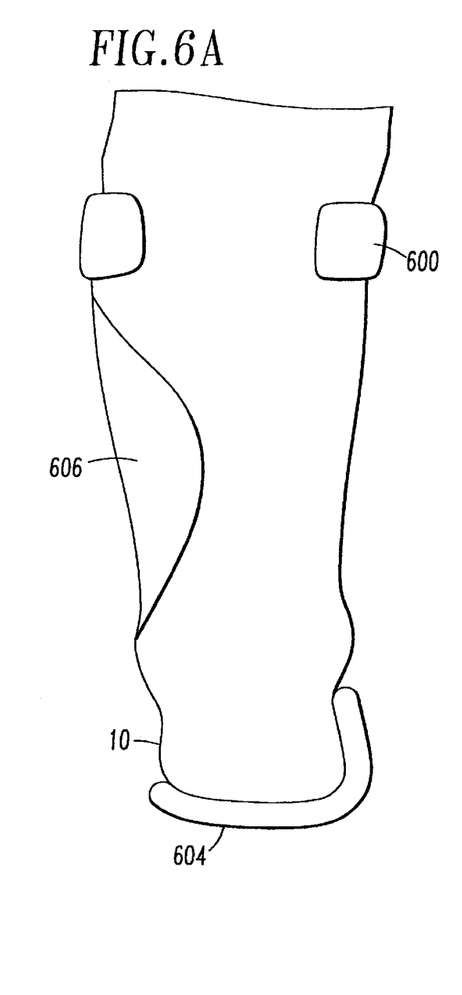
FIGS. 6(A)–6(D) are frontal, lateral, posterior, and medial views, respectively, of an alternative embodiment of the natural foot orthosis of the present invention for controlling varus.
Figure 6B:
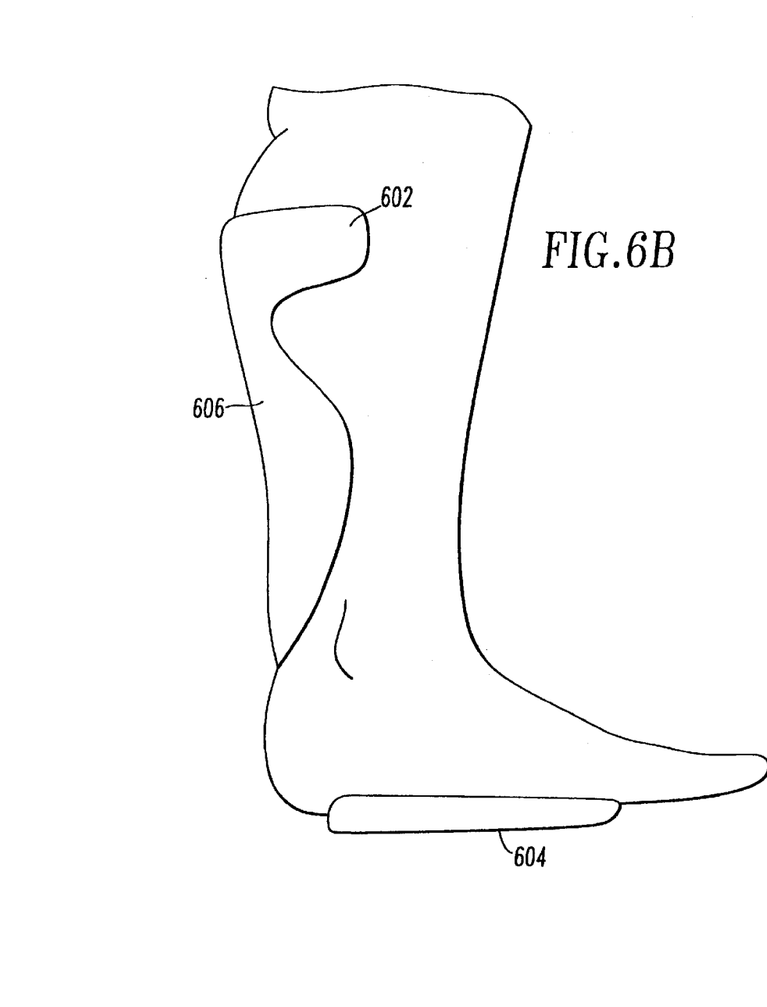
Figure 6C:
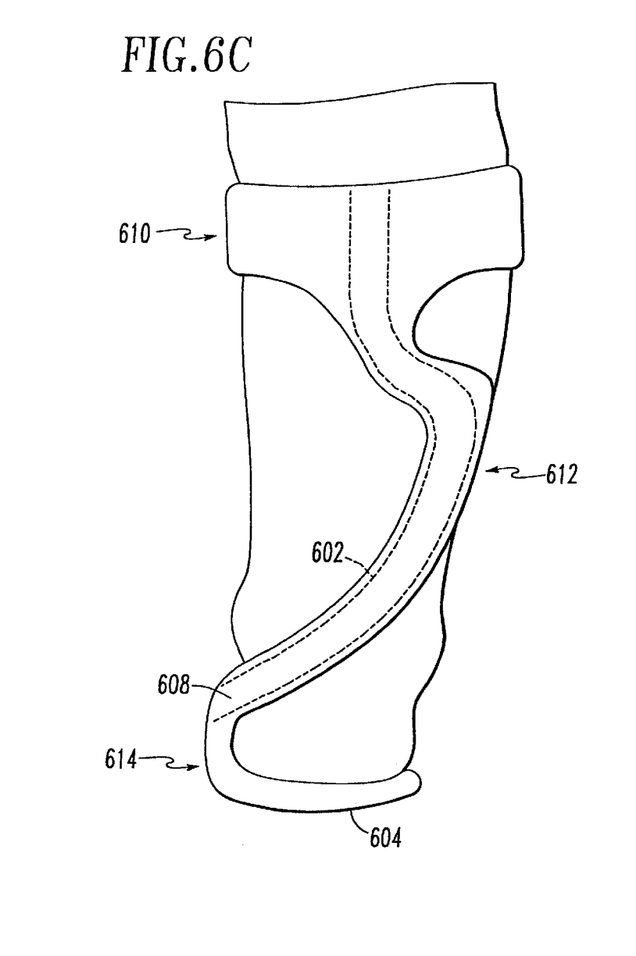
Figure 6D:
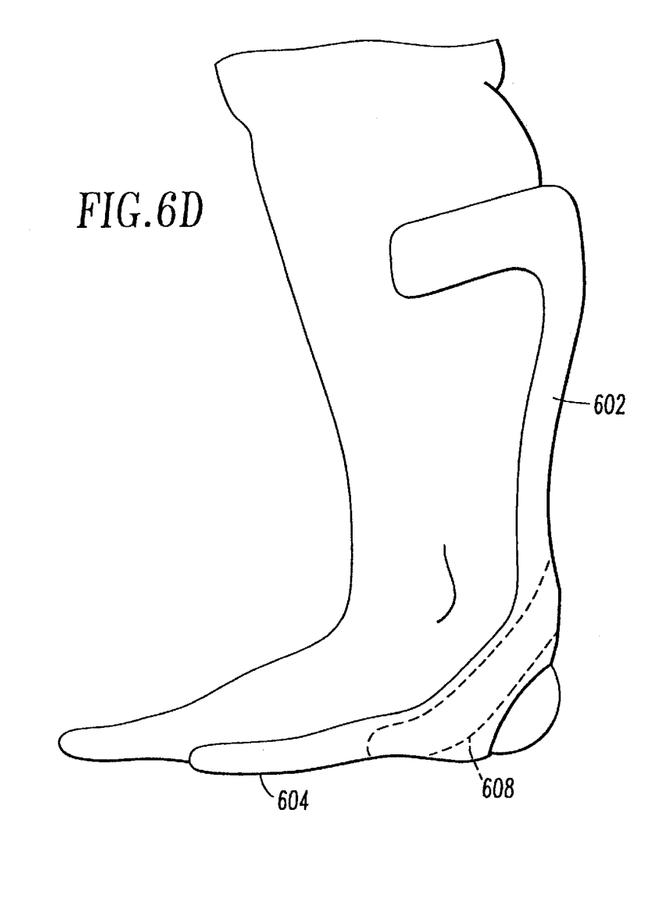

After it has been determined that varus must be controlled using a natural foot orthosis 600, the natural foot orthosis is formed similarly to the N.F.O. with drop foot control with the following modifications. Varus is the resulting position of the foot after inversion occurs. In order to control varus, the N.F.O. with varus control applies three pressure points on the lower extremity to resist inversion, where two pressure points are applied on the medial side of the lower extremity and one pressure point is applied to the lateral side at the point indicated by arrows 610, 612, and 614. The N.F.O. with varus control also provides toe lift assist to also control drop foot.

Figure 7:
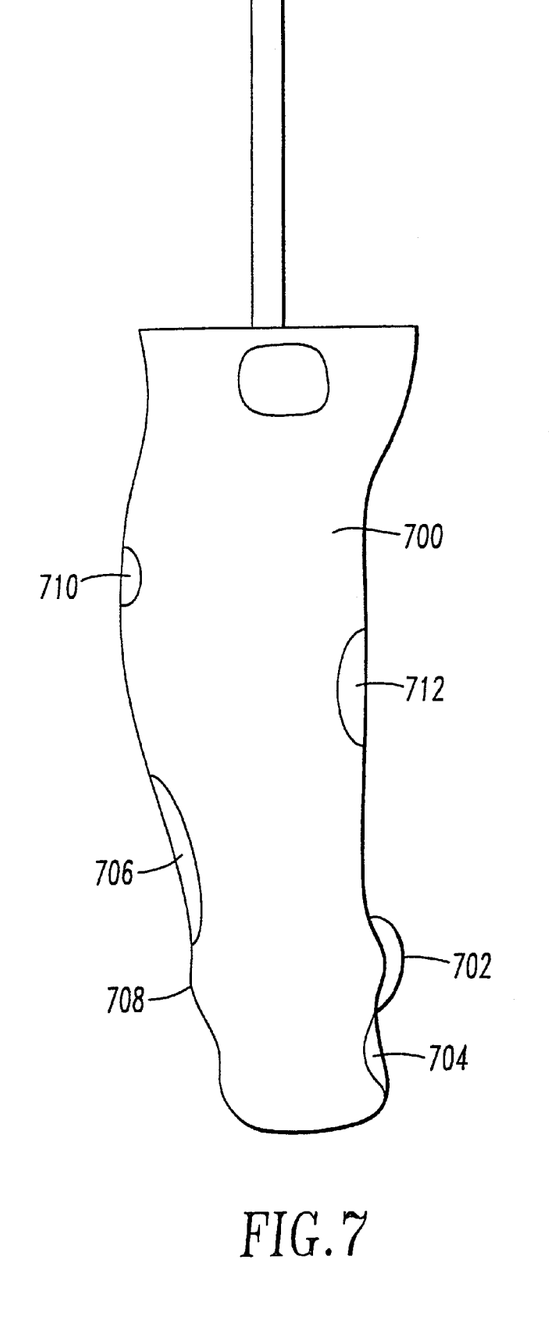
FIG. 7 is a frontal view a positive mold of a right leg of a patient used for forming the natural foot orthosis illustrated in FIGS. 6(A)–6(D).
Figure 8A:
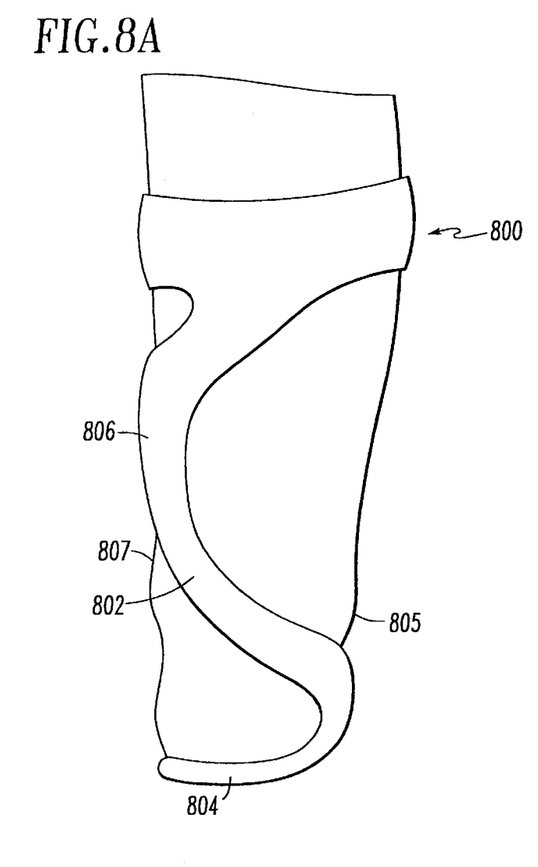
FIGS. 8(A)–8(D) are posterior, medial, lateral, and frontal views, respectively, of an alternative embodiment of the natural foot orthosis of the present invention for controlling valgus.
Figure 8B:
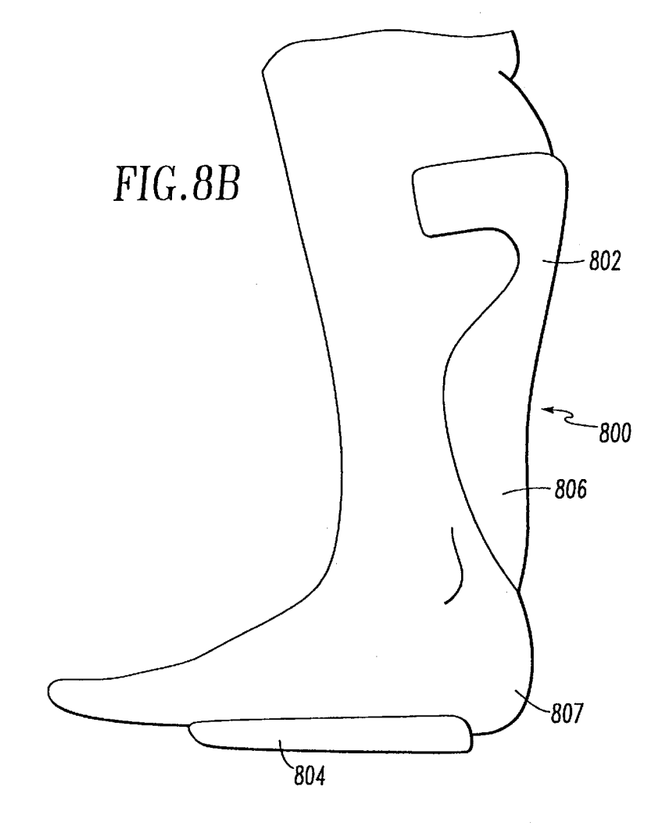
Figure 8C:
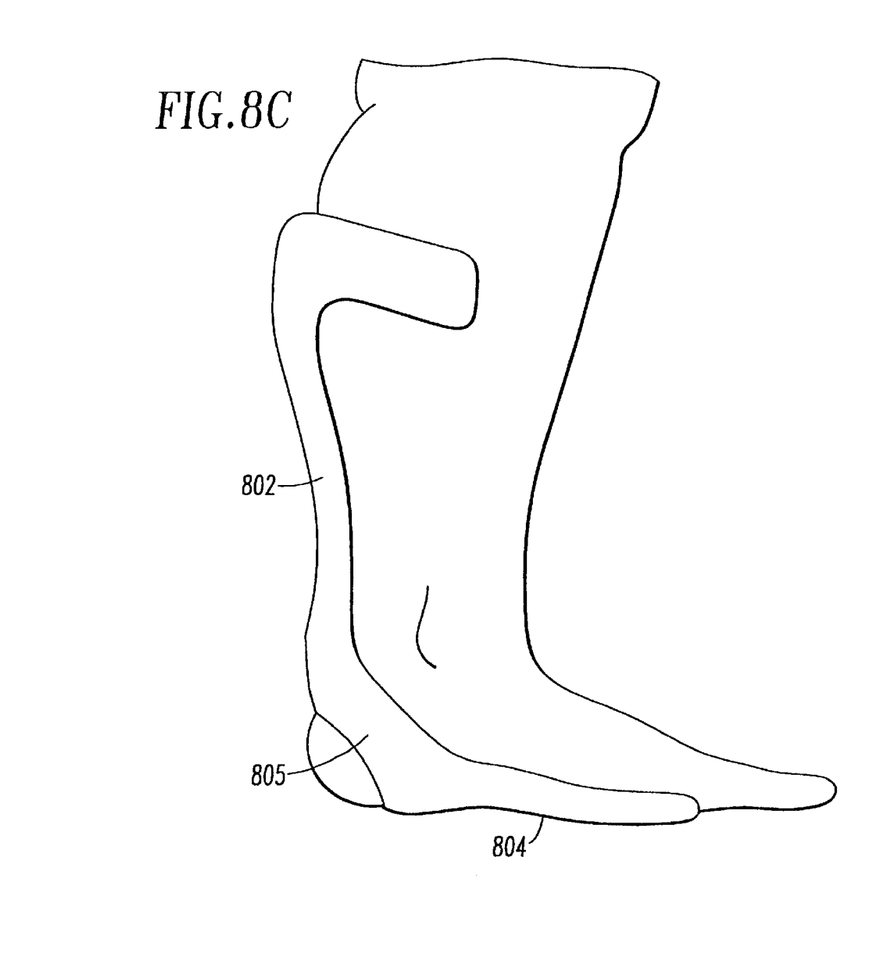
Figure 8D:
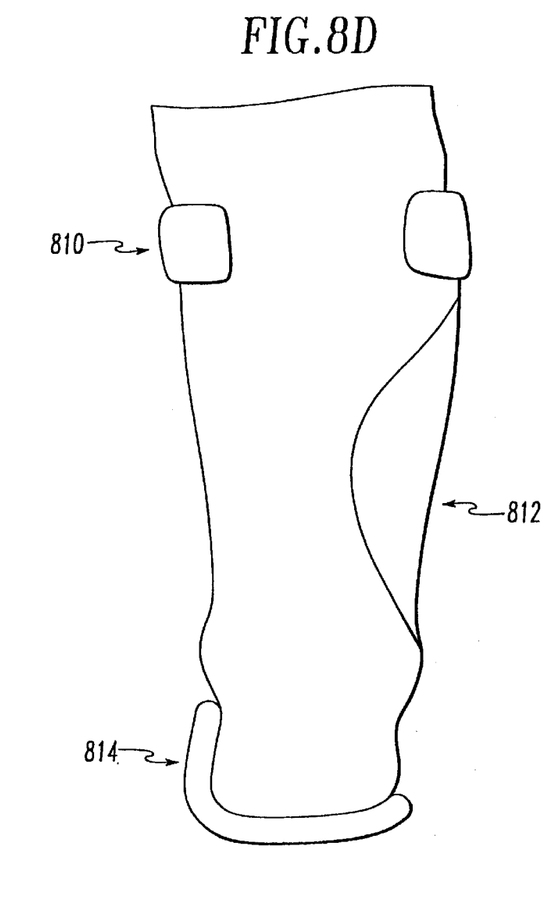

The positive mold 700, as illustrated in FIG. 7 by a frontal view the positive mold of a right leg, is formed similarly as the previous embodiment where the positive mold 700 is modified by adding approximately ⅛ to ¼ inch to the build-up of the mold over the medial malleolus 702. The positive mold is further modified to create the three pressure point system by removing portions of the positive mold: 1) at a point 704 below the medial malleolus 702, making sure not to interfere with the tendon or arch; 2) at a point 706 which two inches above the lateral malleoli 708 and three inches below the fibula head 710, anterior to within one inch of the tibia crest and posterior to midline; and 3) at a point 712 which is 1½ inches distal to the fibula head 710 and two inches wide anterior to within one inch of the tibia crest posterior to midline. Each of the three areas 704, 706, and 712 are removed to form a concavity between approximately ¼ inch to ⅜ inch in the positive mold 700. These three concave points 704, 706, and 712 in the positive mold 700 will create three pressure points by the N.F.O. on the lower extremity, since the N.F.O. will not follow the contour of the lower extremity at these points.

The heated copolymer strip is then positioned on the modified positive mold 700 in the same manner as the previous example, except that the copolymer strip is brought past proximal mid line lateral to within one inch of the tibia crest to start the curve upward by the copolymer strip. The copolymer strip is further medial centered in the medial proximal calf band concavity. The heated copolymer sheet is then drape mold over the positive mold, vacuum sealed, and trimmed in the same manner as the previous example to form the N.F.O. with varus control.

N.F.O. with Valgus Control

In order to control valgus, two pressure points must be created on the lateral side of the lower extremity while another pressure point is created on the medial side of the lower extremity between the two lateral pressure points. An alternative embodiment of the natural foot orthosis 800 of the present invention illustrated in FIGS. 8(A)–(D) achieves these three pressure points through its unique design, wherein FIGS. 8(A)–(D) show posterior, medial, lateral, and frontal views of the natural foot orthosis 800, respectively. As can be seen from the figures, the calf portion 802 of the natural foot orthosis 800 extends upward from foot plate 804 beneath the lateral malleolus 805 and then curves to extend upward along the medial side 807 of the posterior of the lower extremity, wherein a portion 806 of calf portion 802 is extended around the medial side of the lower extremity. As indicated by the dashed lines, a thermoplastic reinforcing strip 808 extends from a longitudinal arch in the foot plate 804 and along the path of the calf portion 802, wherein the thermoplastic reinforcing strip 808 is integrally formed with the thermoplastic material comprising foot plate 804 and calf portion 802. The natural foot orthosis 800 resists inversion of the foot by applying two medial pressure points and one lateral on the lower extremity, as indicated by arrows 810, 812, and 814 in FIG. 6(D).

After it has been determined that valgus must be controlled using a natural foot orthosis 800, the natural foot orthosis is formed similarly to the N.F.O. with drop foot control with the following modifications. Valgus is the resulting position of the foot after eversion occurs. In order to control valgus, the N.F.O. with valgus control applies three pressure points on the lower extremity to resist inversion, where two pressure points are applied on the lateral side of the lower extremity and one pressure point is applied to the medial side, as indicated by the arrows 810, 812, and 814 in FIG. 8(D). The N.F.O. with valgus control also provides toe lift assist to also control drop foot.

Figure 9:
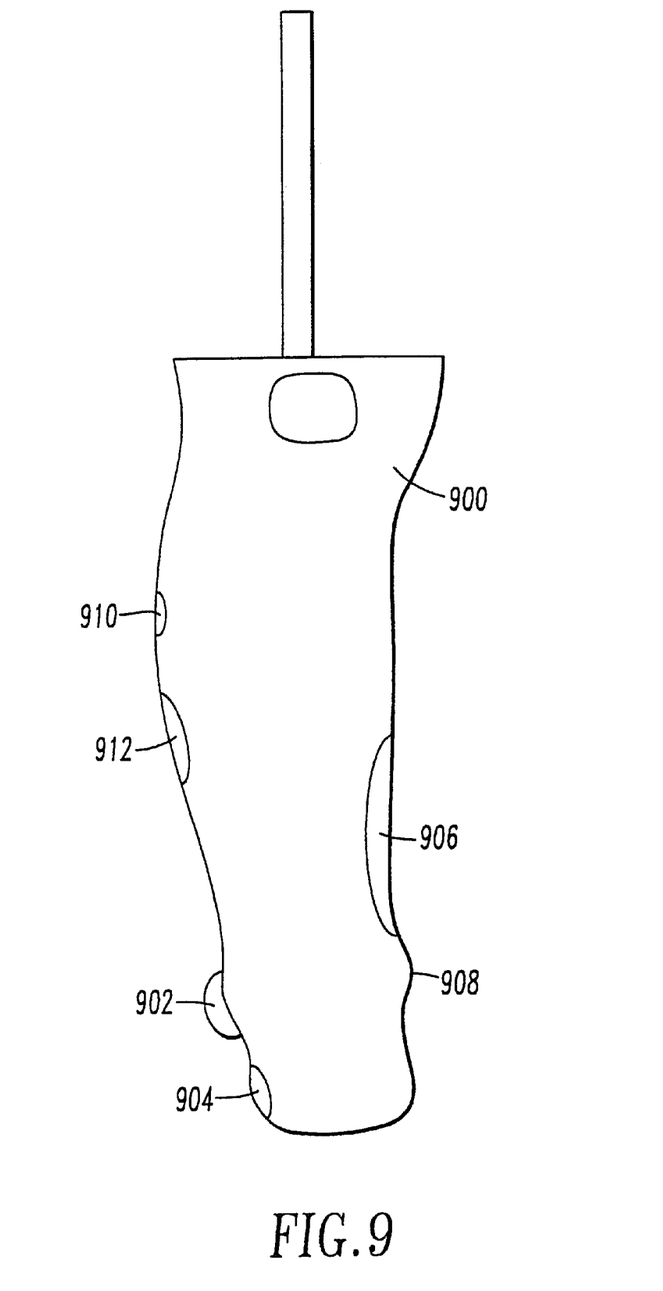
FIG. 9 is a frontal view of a positive mold of a right leg of a patient used for forming the natural foot orthosis illustrated in FIGS. 8(A)–8(D).

The positive mold 900, as illustrated in FIG. 9 by a frontal view the positive mold of a right leg, is formed similarly in accordance with the N.F.O. with drop foot control except that it is modified differently to create the three pressure point system. The positive mold 900 is modified by adding approximately ⅛ to ¼ inch to the build-up of the mold over the lateral malleolus 902. The positive mold 900 is further modified by removing portions of the positive mold 900: 1) at a point 904 below the lateral malleoli 902, making sure not to interfere with the tendon; 2) at a point 906 which is two inches above the medial malleolus 908 and three inches below the fibula head 910, anterior to within one inch of the tibia crest and posterior to midline; and 3) at a point 912 which is 1½ inches distal to the fibula head and two inches wide anterior to within one inch of the tibia crest and posterior to midline. Each of the three areas 904, 906, and 912 are removed to form a concavity between approximately ¼ inch to ⅜ inch in the positive mold 900. These three concave areas 904, 906, and 912 in the positive mold 900 will create three pressure points by the N.F.O. on the lower extremity, since the N.F.O. will not follow the contour of the lower extremity at these points.

The heated copolymer strip is then positioned on the modified positive mold in the same manner as the N.F.O. with drop foot control, except that the copolymer strip is brought past proximal midline medial to within 1 inch of the tibia crest to start the curve upward by the copolymer strip. The copolymer strip is further lateral centered in the lateral calf band concavity. The heated copolymer sheet is then drape mold over the positive mold, vacuum sealed, and trimmed in the same manner as the previous examples to form the N.F.O. with valgus control.

In each of the above-described embodiments, the thicknesses of the copolymer strip and copolymer sheet as well as the depths of the positive mold modifications encompass the optimal design characteristics for normal control of an average lower extremity. However, it is understood that the thicknesses of the copolymer strip and copolymer sheet can be varied to change the desired strength characteristics of the natural foot orthosis 2 depending upon the desired need. Furthermore, the location and depth of the modifications to the positive mold can also be varied to change the location and effect of the pressure points exerted by the natural foot orthosis 2. Therefore, the method for fabricating a natural foot orthosis 2 as set forth above may be utilized for increasing the strength and durability while maintaining the lightness of any design for a natural foot orthosis.

As can be seen from the foregoing, a natural foot orthosis formed in accordance with the present invention will achieve an orthosis that is lighter, cosmetically superior, dynamic, and durable. Moreover, by forming a natural foot orthosis in accordance with the present invention will, strategically positioned copolymer material can be combined to blend together with the structure of the natural foot orthosis to provide predetermined reinforcement areas to increase the strength and functionality of the natural foot orthosis.

What is claimed is:

1. A method of forming a natural foot orthosis for providing support for a lower extremity, comprising the steps of:

forming a positive mold of said lower extremity;

determining locations where additional support is needed for the lower extremity;

positioning a thermoformable plastic material at the locations on said positive mold for providing increased support for the the lower extremity at said locations;

wrapping a thermoformable plastic sheet around said positive mold and said thermoformable plastic material, said thermoformable plastic sheet having a surface area greater than said thermoformable plastic material; and vacuum sealing said thermoformable plastic sheet around said positive mold so that said thermoformable plastic sheet and said thermoformable plastic material bond together.

2. The method of forming a natural foot orthosis for providing support for a lower extremity as defined in claim 1, wherein said thermoformable plastic material and said thermoformable plastic sheet are formed from a co-polymer having a ratio of approximately 90-10 polypropylene to polyethylene.

3. The method of forming a natural foot orthosis for providing support for a lower extremity as defined in claim 1, wherein said thermoformable plastic material and said thermoformable plastic sheet are formed from a co-polymer having a ratio of approximately 93-7 polypropylene to polyethylene.

4. The method of forming a natural foot orthosis for providing support for a lower extremity as defined in claim 1, wherein said thermoformable plastic material is a strip of co-polymer approximately 3/16 inch thick, approximately 24 inches long, and approximately 3¼ wide.

5. A method of forming a natural foot orthosis for providing support for a lower extremity, comprising the steps of:

forming a positive mold of said lower extremity;

forming areas for increased support in said positive mold by modifying the positive mold of the lower extremity at predetermined locations on said positive mold such that said positive mold deviates from a shape of the lower extremity, positioning a thermoformable plastic material around said predetermined locations on said positive mold for providing increased support for the natural foot orthosis at said predetermined locations;

wrapping a thermoformable plastic sheet around said positive mold and said thermoformable plastic material; and vacuum sealing said thermoformable plastic sheet around said positive mold so that said thermoformable plastic sheet and said thermoformable plastic material bond together, wherein said areas of increased support act as pressure points against the lower extremity.

6. The method of forming a natural foot orthosis for providing support for a lower extremity as defined in claim 5, wherein said positive cast is modified by adding approximately 3/16" to the build-up of said positive cast over a medial malleoli section of the positive mold to assist in controlling drop foot.

7. The method of forming a natural foot orthosis for providing support for a lower extremity as defined in claim 6, wherein said thermoformable plastic material is a strip of copolymer including a distal end, wherein said distal end of said strip is centered on a longitudinal arch on said positive mold and said strip is adapted to extend below the malleoli posterior of said positive mold, above the tendon region of said positive mold and curved centered proximal over an edge of said positive mold.

* * * * *